(12) United States Patent
Inaba et al.

(10) Patent No.: US 7,316,770 B2
(45) Date of Patent: Jan. 8, 2008

(54) METHOD OF ELECTROPHORESIS, ELECTROPHORESIS APPARATUS AND CAPILLARY ARRAY

(75) Inventors: Ryoji Inaba, Hitachinaka (JP); Tomoyuki Sakai, Kokubunji (JP); Satoshi Takahashi, Hitachinaka (JP); Muneo Maeshima, Mito (JP); Miho Ozawa, Abiko (JP); Masaya Kojima, Mito (JP); Daizo Tokinaga, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 235 days.

(21) Appl. No.: 09/814,860

(22) Filed: Mar. 23, 2001

(65) Prior Publication Data
US 2002/0023839 A1 Feb. 28, 2002

(30) Foreign Application Priority Data
Aug. 25, 2000 (JP) .............................. 2000-260851

(51) Int. Cl.
*G01N 27/26* (2006.01)
(52) U.S. Cl. ...................... 204/451; 204/601; 204/455; 204/605
(58) Field of Classification Search ................ 204/450, 204/451, 452, 453, 455, 600, 601, 602, 603, 204/604, 605
See application file for complete search history.

(56) References Cited

U.S. PATENT DOCUMENTS

| | | | |
|---|---|---|---|
| 4,985,129 A | 1/1991 | Burd | |
| 5,221,448 A * | 6/1993 | Weinberger et al. | ........ 204/452 |
| 5,366,608 A | 11/1994 | Kambara | |
| 5,516,409 A | 5/1996 | Kambara | |
| 5,529,679 A | 6/1996 | Takahashi et al. | |
| 5,582,705 A | 12/1996 | Yeung et al. | |
| 5,709,727 A | 1/1998 | Bobba | |
| 5,885,430 A * | 3/1999 | Kernan et al. | .............. 204/453 |
| 6,027,627 A * | 2/2000 | Li et al. | .................... 204/603 |
| 6,544,396 B1 * | 4/2003 | Cong et al. | ................. 204/601 |
| 6,562,214 B1 * | 5/2003 | Amrhein et al. | ............ 204/601 |

FOREIGN PATENT DOCUMENTS

JP 10-160705 6/1998

OTHER PUBLICATIONS

"Permeability and Other Film Properties of Plastics and Elastomers," Plastics Design Library (1995).*
Schaffer et al., The Science and Design of Engineering Materials, p. 577 (1995).*
"CEQ™ 2000 DNA Analysis System: Basic Training Workbook," Beckman Coulter, Inc., p. 1-3 (Jun. 2000).*

(Continued)

*Primary Examiner*—Nam Nguyen
*Assistant Examiner*—Jeffrey Barton
(74) *Attorney, Agent, or Firm*—Dickstein Shapiro LLP (57) ABSTRACT

A method of electrophoresis, an electrophoresis apparatus and a capillary array in which a fluorescently labelled sample is supplied into capillaries in a capillary array constituted by a plurality of capillaries and including a sample supply portion, an electrophoresis medium supply portion and a detection portion while controlling the temperature of the capillary array through gas circulation, the sample is caused to migrate and separated in the capillaries through electrophoresis, and at the region where the capillaries are contacted or come close each other a plurality of capillaries are contacted to a solid body so as to dissipate heat generated from the capillaries to the solid body.

20 Claims, 7 Drawing Sheets

OTHER PUBLICATIONS

"Table 4.4.2 Thermal Conductivities of Liquids and Gases," Marks' Standard Handbook for Mechanical Engineers, 10th Ed. (1996).*

"CEQ™ 2000 DNA Analysis System: Basic Training Workbook," Beckman Coulter, Inc., p. 1-9 (Jun. 2000).*

Perena, J.M., "Dynamic Mechanical Relaxations in Polyimide and Polyamideimide." Die Angewandte Makromolekulare Chemie, 106, 61-66. (1982).*

* cited by examiner

METHOD OF ELECTROPHORESIS, ELECTROPHORESIS APPARATUS AND CAPILLARY ARRAY

BACKGROUND OF THE INVENTION

1. Field of the Invention

The present invention relates to an electrophoresis apparatus, a method of electrophoresis and a capillary array in which a sample such as DNA labelled by a fluorescent material is separated, and such as base sequence thereof is detected and analyzed through electrophoresis in a plurality of capillaries.

2. Conventional Art

Electrophoresis using capillaries has been used for the purpose of such as determining base sequence and base length of DNA. A method of multi capillary electrophoresis using a plurality of capillaries is already known broadly and is disclosed in many patent documents. U.S. Pat. No. 5,366,608 discloses to increase density of capillaries at a detection portion of fluorescence from a fluorescently labeled sample in the capillaries than the capillary density at a sample introduction portion. U.S. Pat. Nos. 5,516,409 and 5,529,679 disclose to detect fluorescence from a fluorescently labeled sample to be discharged from capillaries in combination with the capillaries and flow cells. U.S. Pat. No. 5,582,705 discloses to dispose a detection portion of a capillary array on a mount, to remove a part of coating on the capillaries to form a light transmission portion for the capillary array and to irradiate laser beam from the side face of the light transmission portion to detect fluorescence. U.S. Pat. No. 5,790,727 discloses to dispose optical fibers at a detection portion of a capillary array to detect fluorescence wherein the vicinity of the detection portion of the capillary array is closely contacted to a V shaped groove assembly.

U.S. Pat. No. 4,985,129 discloses to dispose a single piece of a capillary wound in a coil shape in a housing and to provide a heat dissipation member in a room surrounding the capillary. However, the document does not take into account of a problem of heat concentration in a multi capillaries.

In an electrophoresis separation and analysis, a sample containing DNA which is the very object of measurement is injected into gel such as polyacrylamide in a glass capillary and a voltage is applied between both end portions of the capillary. DNA compounds in the sample migrate in the capillary and are separated depending on such as molecular weight thereof to produce DNA bands in the capillary. Since a fluorescent dye is added to the respective DNA bands, the respective DNA bands are colored through irradiation of laser beam, therefore, the color is read with a fluorescent detection means to determine DNA sequence. Herein, in order to enhance resolution of DNA through electrophoresis it is important to keep the capillary at a predetermined temperature, for example, at 50° C. over the entire period of electrophoresis. This is because the migration speed of DNA in gel has to be kept constant at the above predetermined temperature.

As temperature control methods of capillaries in a capillary electrophoresis apparatus, the following methods have been used, in that a contact temperature adjustment method in which the capillaries are contacted to a temperature control plate provided in the electrophoresis apparatus; an air conditioning method in which temperature adjusted gas such as air is circulated in a thermostatic oven provided in the electrophoresis apparatus and the capillaries are disposed in the temperature adjusted gas so as to adjust the temperature of the capillaries; and a liquid temperature adjustment method in which temperature adjusted liquid such as water is circulated in a vessel provided in the electrophoresis apparatus and the capillaries are disposed in the temperature adjusted liquid so as to adjust the temperature of the capillaries.

The contact temperature adjustment method in which the capillaries are directly contacted to the temperature control plate provided with a heating and cooling device such as Peltier elements shows an advantage that Joule's heat generated at the capillaries during electrophoresis is effectively removed from the capillaries. However, since a fine temperature variation of the temperature control plate is directly transmitted to the capillaries, it is necessary to control the temperature of the temperature control plate strictly at a predetermined temperature. However, a temperature variation could not be avoided, because a power source is frequently turned on and off for the temperature control.

The liquid temperature adjustment method shows an advantage that the Joule's heat generated at the capillaries is effectively removed from the capillaries. However, since the liquid has to be circulated in the apparatus which complexes the apparatus and increases the cost thereof.

The gas circulation method, for example, the air conditioning method and the air circulation method shows advantages that the structure of the electrophoresis is simple and further because of existence of air between the capillaries and a heater portion in the thermostatic oven an influence of heater temperature fluctuation affected on the capillaries is relaxed. However, since the heat conduction from the capillaries to air is small, the heat dissipation of the Joule's heat generated from the capillaries is insufficient. The insufficient heat dissipation from the capillaries will affect the electrophoresis speed and causes an adverse effect to the analysis result.

SUMMARY OF THE INVENTION

Accordingly, an object of the present invention is to provide a method of electrophoresis, an electrophoresis apparatus and a capillary array which can effectively dissipate or draw out heat generated in the capillaries.

The present invention provides a method of electrophoresis in which and a fluorescently labelled sample is supplied into capillaries in a capillary array constituted by a plurality of capillaries and including a sample supply portion, a gel supply portion and a detection portion located between the both, while forming a gas flow between the capillary array and a heating and cooling means for controlling the temperature of the capillary array and controlling the temperature of the capillary array, the sample is caused to migrate and separated in the capillaries through electrophoresis, and at least a part of the region where the capillaries are contacted or come close each other a plurality of capillaries are contacted to a solid body so as to dissipate heat generated from the capillaries to the solid body. The capillary array temperature control includes Peltier elements for heating and cooling the capillary array and a gas circulation means such as a fan which provides a gas circulation flow for the capillary array. Further, the capillary array is disposed in the thermostatic oven so as not to directly contact to the heating and cooling means. Still further, since the fan is provided in the thermostatic oven, the Joule's heat generated in the capillaries is controlled through circulation of air. The temperature in such thermostatic oven generally varies due to frequent switching on and off of the heating and cooling means such as Peltier elements. Therefore, if the capillary array directly contacts to a heating source/cooling source, the temperature of the capillary array fluctuates which causes an adverse effect to resolution of separation and analysis through electrophoresis. In the present invention, through formation of circulating gas flow between the capillary array and the heating and cooling means the heating and cooling energy from the heating and cooling means is transmitted to the capillary array via the gas flow. Further, since the heat conduction between the capillary array and the gas flow is very poor, through contacting a solid body having a better heat conductivity than the gas to the capillary array the heat dissipation and cooling of the capillary array is accelerated, thereby, the temperature of the capillary array can be controlled accurately.

The interval between the capillaries in the capillary array at the sample introduction portion is spaced apart, however, the interval thereof at a fluorescent detection portion is narrowed and the capillaries are arranged in such a manner that the capillaries contact or substantially contact each other and are aligned on one plane to form a coplanar region. Then, a part of the coating (polyimide) on the capillaries at the coplanar region is removed so as to permit laser beam irradiation from the outside on to the fluorescently labeled sample in the capillaries. In the lateral direction of the coplanar a wave guide portion having light transmission property is formed. Light such as laser beam is irradiated one or both directions of the wave guide portion and the fluorescently labeled sample in the capillaries is irradiated to emit fluorescence. Therefore, an on-column irradiation method is preferable in which the light is irradiated to the portion where the coating on the capillaries is removed. However, the present invention is also applicable to other laser irradiation methods than the on-column method such as sheath flow method and scanning method. Near the detection portion it is preferable to contact the solid body to the capillaries so as to surround substantially the outer circumference of the capillaries or, if necessary, to form a light wave guide passage. Thereby, the Joule's heat generated in the capillaries is desirably drawn out to the outside. It is necessary that the heat conductivity of the solid body is higher than that of air. Further, it is preferable that the heat capacity of the solid body is large so as to permit the heat from the capillaries to diffuse into the solid body. Through circulation of gas flow between the solid body and the heating and cooling means the heat is transferred to capillary array and is removed therefrom.

Further, the gel supply portion, detection portion and the vicinity of the detection portion can be surrounded by the solid body. Thereby, the heat at the portion where the capillaries are collected is effectively drawn out to the outside. When surrounding the capillaries with the solid body, percentages in the effect of enhancing the resolution in electrophoresis at capillary collected region at one side of the detection portion, at capillary collected portion at the other side of the detection portion and other region are about 40:40:20. It is effective to enhance the resolution in the electrophoresis, if the heat in the former two regions among the three regions is effectively dissipated. Further, it is preferable that the above solid body includes at least one material selected from metal, polymer material and inorganic material. These materials can be used alone or in combination. In particular, it is preferable to add a variety of inorganic filler materials in a polymer material so as to improve heat conductivity. For example, inorganic powders such as silica, alumina and titania powders and metal powder such as copper powders can be used.

Still further, when resin such as gluing agent is applied between the solid body and the outer surface of the capillaries, the gaps therebetween are eliminated or substantially reduced, thereby, the heat from the capillaries can effectively drawn out. An inorganic or metal powder having a high heat conductivity can be added to the resin.

The present invention provides a method of electrophoresis in which the temperature of a capillary array is controlled by a heating means and a gas flow, a sample is caused to migrate in the capillaries through electrophoresis and is separated, capillaries contacting the gas flow are spaced apart from the heating means and the gas flow is formed between the capillaries and the heating means, thereby, temperature control of the capillaries is performed. Further, the present invention provides a method of electrophoresis in which the capillaries contacting the gas flow are spaced apart from the heating and cooling means, the capillaries are contacted to the solid body and gas flow is flown between the capillaries and the heating and cooling means, thereby, the temperature control of the capillaries is performed.

Further, the present invention provides an electrophoresis apparatus which includes an capillary array having a plurality of capillaries and including a sample supply portion, a gel supply portion and a detection portion, means for heating and cooling the capillary array, means for forming a gas flow between the capillary array and the heating and cooling means and means for applying a voltage to a sample in the capillaries. Still further, the present invention provides an electrophoresis apparatus which includes a capillary temperature control means of gas circulation type, means for applying a voltage to the sample in the capillaries and a solid body contacting the outer circumferences of the capillaries at a region where the capillaries contact or come close each other. Still further, the present invention provides an electrophoresis apparatus which includes a solid body contacting the outer circumferences of the capillaries located at the gel supply portion, the detection portion and at the vicinity thereof. Still further, the present invention provides an electrophoresis apparatus which includes, a capillary array constituted by a plurality of capillaries having a sample supply portion, a gel supply portion and a detection portion, a gas circulation type capillary temperature control means, means for applying a voltage to a sample in the capillary array, means for heating and cooling the capillary array and means for supporting the capillary array while being spaced apart from the heating and cooling means. Still further, the present invention provides an electrophoresis apparatus which includes a solid body contacting to the outer circumferences of capillaries at the gel supply portion and the detection portion and at the vicinity thereof.

In the above apparatus, it is preferable that the solid body is made of a material having a higher heat conductivity than air, and the solid body is contacted to the capillaries so as to surround substantially the outer circumferences of the capillaries. Further, it is preferable that the solid body is arranged so as to surround the detection portion and the vicinity thereof. Still further, it is preferable that the solid body contains at least one selected from a metal, a polymer material and an inorganic material. Still further, the solid body can be a resin applied on the outer surface of the capillaries. The resin can contain inorganic powders or metal powders having a higher heat conductivity than the resin.

The present invention provides a capillary array which includes a plurality of capillaries, a sample supply terminal located at one end portion of the capillaries, a detection portion, and a solid body contacting the capillaries at least a part of a region where the capillaries contact or come close to each other. Further, the present invention provides a capillary array which includes a plurality of capillaries, a sample supply terminal located at one end portion of the capillaries, a detection portion, and a solid body contacting the capillaries at least a part of a region where the capillaries contact or come close to each other, and a region where the capillaries are spaced apart from each other. Further, the present invention provides a capillary array which includes a solid body contacting to at least a part of the capillaries near the detection portion. Still further, the present invention provides a capillary array which includes a solid body contacting to the capillaries near the detection portion. With regard to the solid body material, the polymer material and the resin material explained in connection with the capillaries, the explanation made for the above electrophoresis method and the electrophoresis apparatus can also be applied.

Among the entire length region of the capillaries the region where the capillaries contact each other is placed in a condition where the Joule's heat generated from the capillaries is hard to dissipate. Through contacting the solid body to the capillaries at such region the Joule's heat generated from the capillaries is effectively dissipated. It is preferable that the solid body contacting the capillaries is made of a material having a higher heat conductivity than air. A metal plate such as copper plate and aluminum plate can be used therefor. However, when sandwiching the capillaries only with metal plates, contacting area between the capillaries and the metal plates can be limited to reduce heat conduction, therefore, in order to avoid such possible drawback, a polymer material such as rubber having a large elasticity and a large heat conductivity can be inserted between the capillaries and the metal plates, thereby, the contacting area with the capillaries can be increased. Further, even if the heat conductivity of the rubber to be inserted between the capillaries and the metal plates is not so large but if the thickness thereof is thin, such rubber can be used. Of course, filler powders having a high heat conductivity can be add to the rubber. Such rubber having a high heat conductivity is already marketed. Further, present invention provides a capillary array with a capillary securing means for preventing the capillaries from contacting each other in a region where the capillaries are not sandwiched by the solid body among the region of capillary entire length. With the provision of the capillary securing means for preventing the capillaries from contacting each other the gas volume contacting the capillaries by means of the gas circulation means is increased, thereby, the Joule's heat generated from the capillaries is effectively dissipated.

Further, the present invention provides a capillary array which is used in an electrophoresis apparatus including the gas circulation type capillary temperature control means wherein the space between the capillaries is filled with a solid body such as a polymer and metal. With a conventional gas circulation type capillary temperature control means, the gas volume contacting to the capillaries is small, in particular, in the region where the capillaries gather collectively, therefore, the heat dissipation there is insufficient. When the space for the gas in such region is eliminated and is instead filled with a solid body, the Joule's heat is effectively dissipated. As a heat transmission medium for the Joule's heat a metal having a large heat conductivity is preferable, but such as resin can be used. A structure in which the capillaries are secured with such as molding resin can be used. Further, after burying the capillaries into resin and when metal plates are contacted to the resin, the heat is further effectively dissipated. When a metal plate is used as a heat transmission medium, it is preferable to interpose an insulative material between the surface of the metal plate and the capillaries for preventing a possible short circuiting between the inside of the capillaries and the metal plate.

The above capillary array is provided with a heating and cooling means such as Peltier elements and is attached within a thermostatic oven with a space portion for permitting gas circulation. In the space at least one fan preferably two fans are provided for causing gas flow for the capillary array. The capillary array is disposed so as not to directly contact to the heating and cooling means. The capillary array is disposed while being spaced apart from the heating and cooling means or an inner wall face of the thermostatic oven where the heating and cooling means is arranged, and a space permitting gas flow is formed between the capillary array and the heating and cooling means or the inner wall face. In order to efficiently discharge the Joule's heat generated from the capillaries a solid body having a desirable heat conductivity, for example, an aluminum plate having thickness of 1 mm is contacted to the capillary portion in the thermostatic oven.

Near the detection portion of the capillary array, the capillaries are concentrated, for example, near the outlet from the thermostatic oven, the capillaries contact or come close each other. Therefore, at such portion the Joule's heat concentrates which affects such as electrophoresis speed. Therefore, at this portion (near the detection portion) either a solid body having a high heat conductivity such as polymer and metal is contacted to the capillaries or the solid body is contacted to the capillaries so as to surround the same, thereby, heat dissipation is accelerated.

The present invention provides an electrophoresis apparatus with a gas circulation type capillary temperature control means and a capillary array used for an electrophoresis apparatus in which the Joule's heat generated at the capillaries is not directly transferred to gas but is heat-conducted to a solid body having a larger surface area than that of the capillaries, then the heat is transferred to the gas from the solid body. In this structure, since the heat generated from the capillaries is once heat-conducted to a medium having a larger surface area and then the heat is dissipated to air from the above medium having a large contacting area with air, the heat conduction from the capillaries to air is extremely increased. Therefore, in one sense, the present invention can be defined as an air conditioning-contacting parallel use method.

The heat conducting medium means for contacting the capillaries either can be formed as one belonging to the side of the apparatus or, after forming a combination of capillaries and the heat conducting medium means, the combination can be attached to the apparatus. Further, the heat conducting means can be a part of the capillaries such as one adhered to the capillaries through a gluing agent. The region of the capillaries contacting to the heat conducting medium can be all over the capillaries or a part of the capillaries. Since heat generation amount per unit area is significant, in particular, near the detection portion where the capillaries gather collectively and contact each other and at the ends of the capillary array, it is effective if the heat conducting medium is attached these regions. In the regions other than the region between the fluorescent detection and the sample introduction terminal in the capillaries, it is necessarily required to keep the migration speed of DNA in the gel constant, therefore, it is necessary to keep the temperature of the capillaries at the regions at such high temperature of 50° C. However, even in such regions if dissipation of the Joule's heat is insufficient, a resolution by electrophoresis can be deteriorated. Accordingly, if the capillaries are contacted to the heat conducting medium in the regions other than the region between the fluorescent detection portion and the sample introduction terminal, the resolution can be enhanced. However, in such instance, it is unnecessary to keep the heat conducting medium at such high temperature of 50° C., it is simply sufficient, if the capillaries are contacted to the heat conducting medium.

Further, even in the region between the fluorescent detection portion and the sample introduction terminal, if the region of the capillaries where the heat conducting medium is contacted is short in comparison with the entire length of the capillaries, it is enough if the heat conducting medium is simply contacted to the capillaries, and it is unnecessary to perform temperature adjustment of the heat conducting medium by the circulation gas. Accordingly, it is acceptable if the heat conducting medium is contacted to the capillaries at the region from the fluorescent detection portion toward the sample introduction terminal (cathode terminal) where the capillaries are gathered collectively, and in this instance it is unnecessary to perform temperature adjustment of the heat conducting medium by the circulation gas. As conditions of the heat conducting medium (or heat bath) which unnecessitate the temperature adjustment by the circulation gas, one having a large heat conductivity, a large volume and a large heat capacity is desirable.

DETAILED DESCRIPTION OF THE EMBODIMENTS

Embodiment 1

Figure 2:
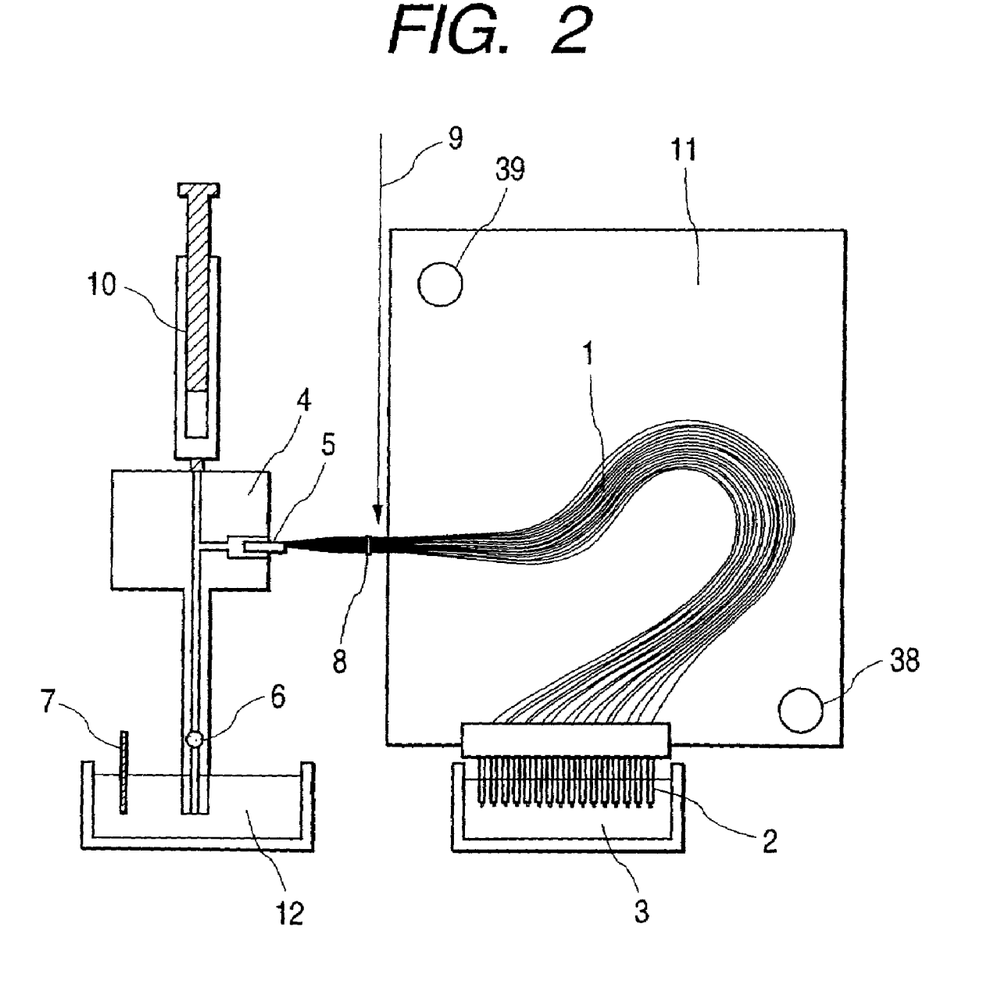
FIG. 2 is a schematic view of an electrophoresis apparatus with a gas circulation type capillary temperature control means to which the present invention is applied.

FIG. 2 shows an electrophoresis apparatus with a gas circulation type capillary temperature control means to which the present invention is applied. At one end of a capillary array 1 an electrode (a sample introduction terminal) 2 is formed which permits an application of a negative voltage. When injecting DNA the cathode 2 is immersed into a solution containing DNA sample, and when performing electrophoresis of the injected sample, the cathode 2 is immersed into buffer solution 3, thereafter, a negative voltage is applied to the cathode 2.

At another end of the capillary 1, a connecting portion 5 for a gel block 4 functioning as means for injecting gel serving as electrophoresis medium into the capillaries is formed. When filling the gel serving as electrophoresis medium into the capillaries, a valve 6 is closed and through pushing down a syringe 10 the gel in the syringe 10 is injected into the capillaries. When performing the electrophoresis, the valve 6 is opened and a predetermined voltage is applied between the cathode 2 immersed in the buffer solution 3 and a grounding electrode 7 immersed in a buffer solution 12.

Figure 3A:
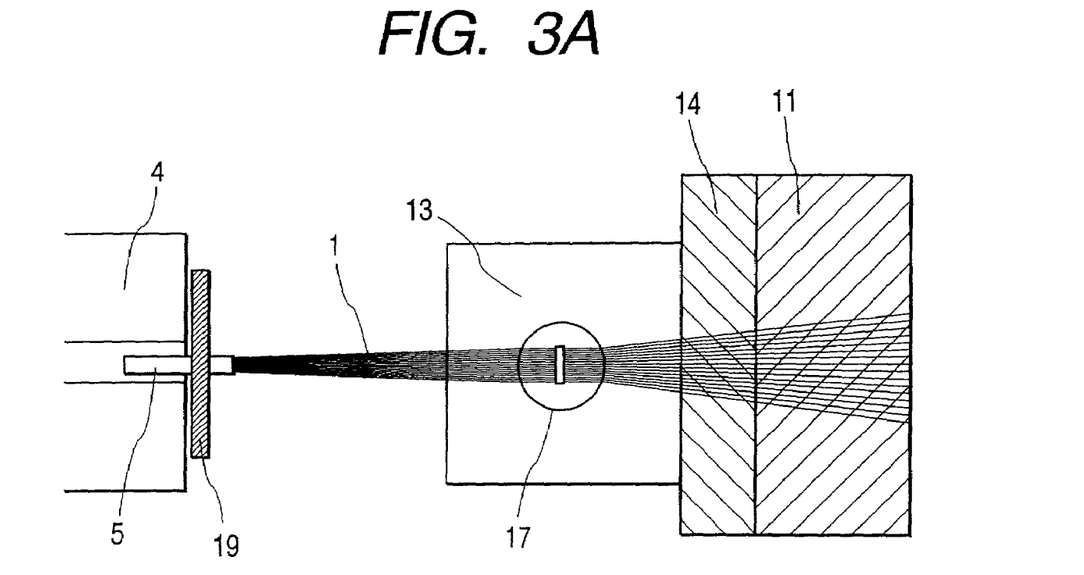
FIG. 3A is a front view of a detection portion and near the same in FIG. 2
Figure 3B:
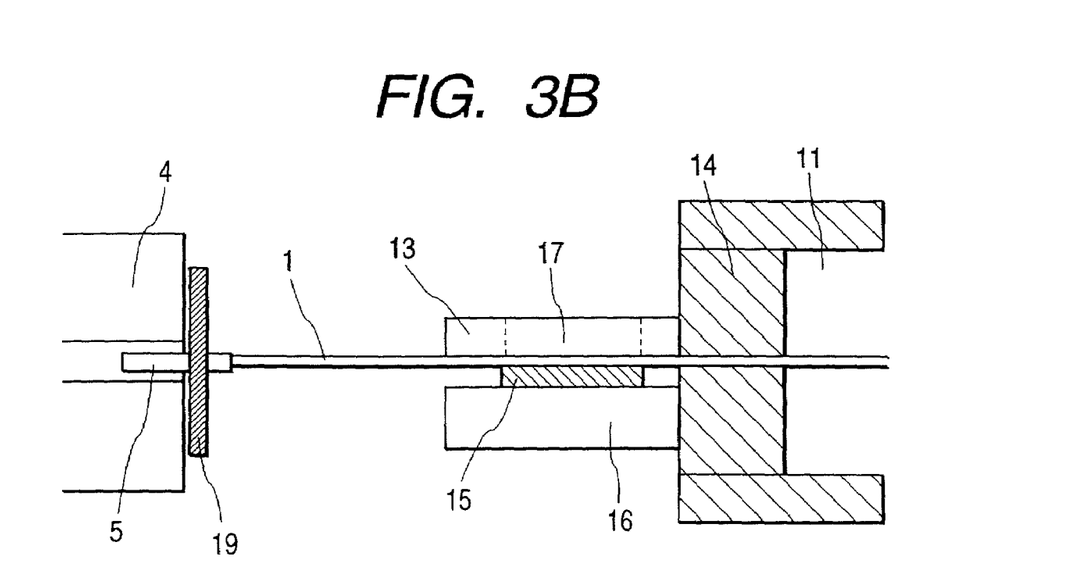
FIG. 3B is a top view thereof.

After irradiating laser beam 9 to a fluorescent detection portion 8 in the capillary array 1 and observing fluorescence generated from the detection portion 8, DNA is detected. Although the capillaries are covered by a polymer thin film, the polymer coating of the capillaries at the detection portion 8 is removed and quartz of the capillaries is exposed. FIG. 3A shows a front view of and near the detection portion and FIG. 3B is a top view thereof. The detection portion 8 of the capillary array 1 is formed on an array stand 15, which is secured to the electrophoresis apparatus via an array holder 13 and a holder cover 16. The fluorescence is detected through a fluorescent detection window 17.

The detection portion is contacted is a wall 14 of a thermostatic oven. Further, the connection terminal 5 for the gel block 4 is secured to the gel block 4 via a stopper member 19. When performing electrophoresis, the capillary array 1 is kept at a predetermined contact temperature by means of a gas circulation type thermostatic oven 11. Air in the thermostatic oven 11 is circulated by fans 38 and 39, thereby, the heat in the capillary array 1 is dissipated.

Herein, the measurement object is a DNA sample having known base length so called size marker, and the temperature in the thermostatic oven is at 60° C., and a voltage applied to the capillaries is 319 V/cm. One of indexes representing DNA resolution in the electrophoresis apparatus is a cross over point (COP), which implies a base length in which spacing equivalent to one base in the detection portion is equal to the full width at half maximum and the larger the value of which is, the higher the resolution of the electrophoresis.

Figure 1A:
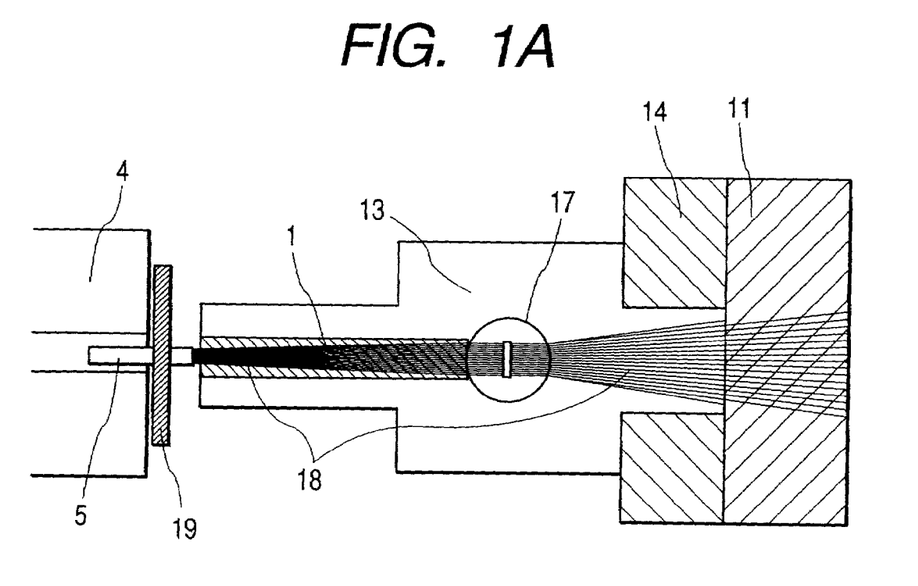
FIG. 1A is a front view of a detector and therearound of an electrophoresis apparatus, and a detection portion and therearound of a capillary array of an embodiment 1 according to the present invention.
Figure 1B:
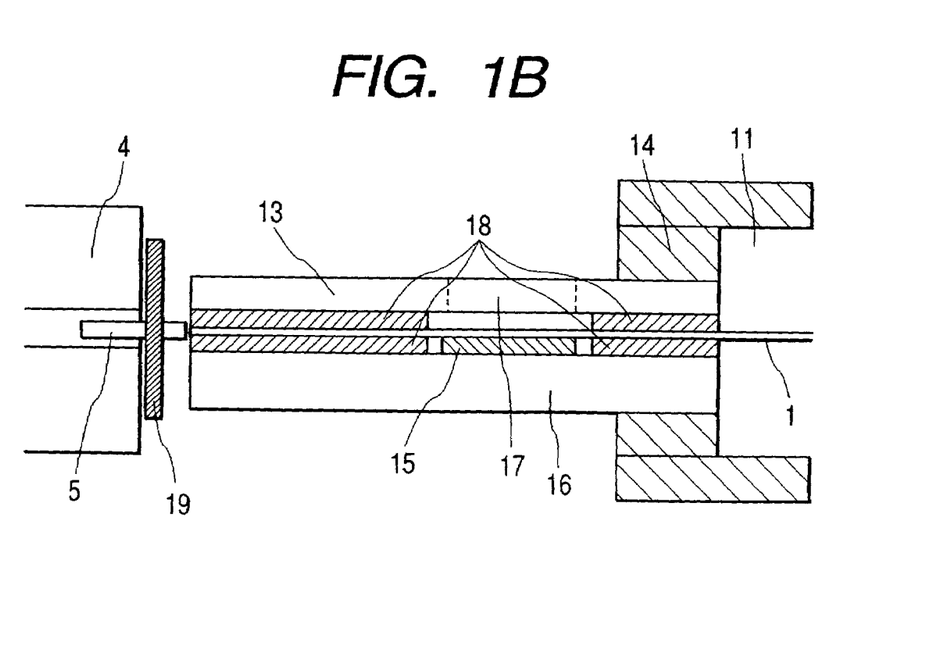
FIG. 1B is a top view thereof.

FIG. 1A shows a front view of an electrophoresis apparatus (only the detector and therearound are illustrated) and the capillary array of an embodiment according to the present invention and FIG. 1B is a top view thereof. At a region between the gel block terminal and the detection portion and a 5 cm region from the detection portion to the wall of the thermostatic oven the capillaries are placed in a concentrated state in which the capillaries are contacted each other. In these regions, the capillaries are sandwiched between the array holder 13 and the holder cover 16 both made of aluminum via a heat conductive rubber sheet 18 filled with inorganic powders.

When the electrophoresis apparatus and the capillary array having the above explained structure is used, the COP was 330 bases. With the present invention an enhancement in resolution of about 80 bases can be achieved in comparison with the COP when no rubber sheet and no aluminum made capillary holder were used.

In the present embodiment, the heat conducting medium is simply contacted to the capillaries in the region between the fluorescent detection portion and the cathode terminal (the sample introduction terminal) and no capillary temperature control is performed. Since the ratio of the length (5 cm) in which the capillaries are contacted to the nontemperature adjusted heat conducting medium with respect to the length (36 cm) between the fluorescent detection portion and the sample introduction terminal is small, therefore, if the non-temperature adjusted heat conducting medium is contacted to the capillaries in the region between the fluorescent detection portion and the sample introduction terminal, an influence affecting to the resolution of the electrophoresis is presumed to be negligibly small.

Embodiment 2

Figure 4A:
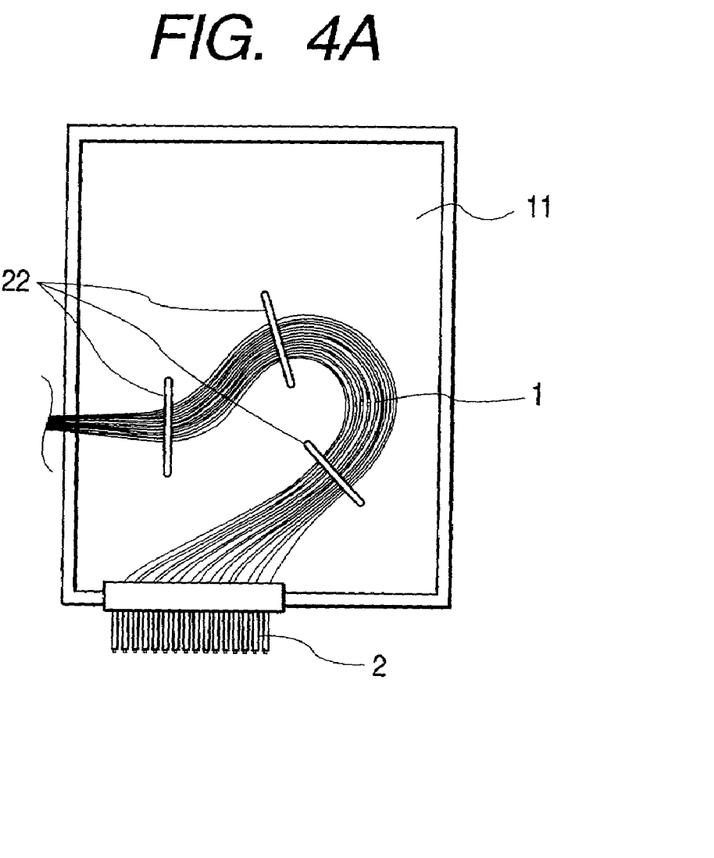
FIG. 4A is a view showing a thermostatic oven of an electrophoresis apparatus representing an embodiment 2 of the present invention.
Figure 4B:
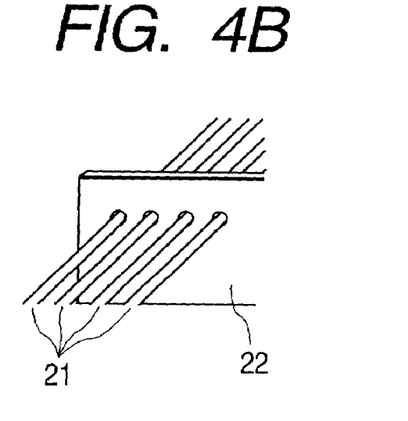
FIG. 4B is a view showing a capillary support means in FIG. 4A
Figure 4C:
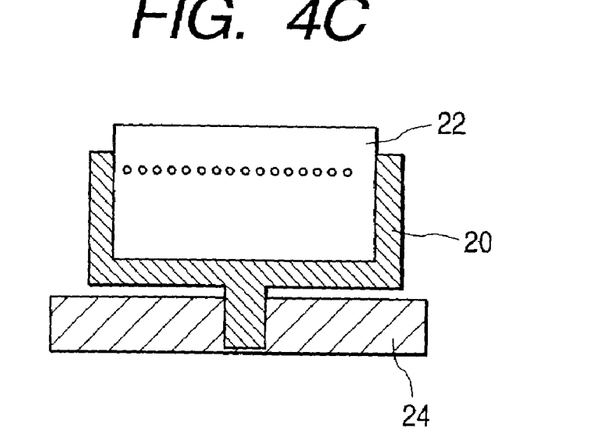
FIG. 4C is a view showing an attachment means for the capillary support means in FIG. 4B.

FIGS. 4A, 4B and 4C show schematic diagrams of the embodiment 2. In a way substantially the same arrangement as in the embodiment 1, in order to avoid contacting of capillaries 21 each other in the thermostatic oven 11, the capillary array 1 is provided with a capillary holding means 22 and further a wall 24 of the thermostatic oven 11 is provided with an attachment means 20 for securing the capillary holding means 22. The capillary holding means 22 are provided at three portions in the thermostatic oven 11 as shown in FIG. 4A. Further, as shown in FIG. 4B with the capillary holding means 22 and the attachment means 20, the mutual contacting of the capillaries 21 as well as the contacting of the capillaries 21 to the inner wall 24 of the thermostatic oven 11 are prevented. FIG. 4C shows details of the wall 24 of the thermostatic oven 11, the capillary holding means 22 and the attachment means 20. With the above measure, the gas volume contacting the capillaries 21 is increased in the gas circulating type thermostatic oven 11, thereby, the Joule's heat generated at the capillaries 21 is effectively dissipated.

When the thus constituted electrophoresis apparatus and capillary array is used, the COP was 340 bases. According to the present embodiment in which a plurality of capillary holding means 22 and of attachment means 20, an enhancement in resolution of about 90 bases can be achieved in comparison with the capillary array with no such means.

Embodiment 3

Figure 5A:
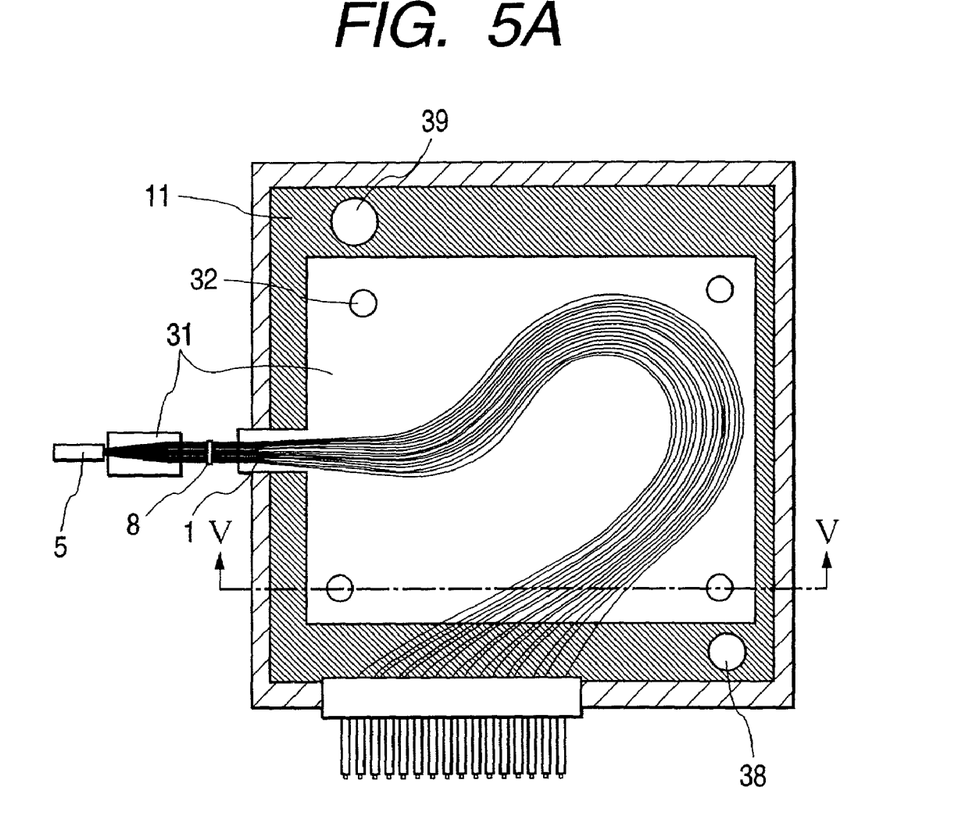
FIG. 5A is a front schematic view of a capillary array of an embodiment 3 of the present invention and FIG. 5B is a cross sectional view taken along the dotted line V-V in FIG. 5A.
Figure 5B:
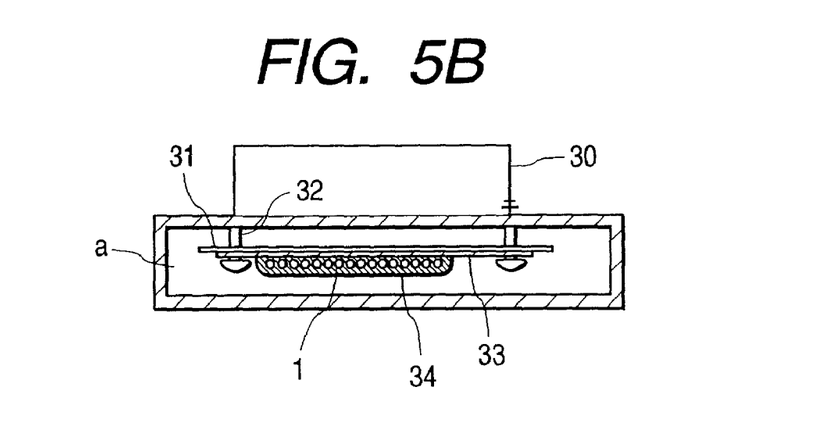

FIG. 5A shows a schematic front view of a capillary array representing an embodiment 3 of the present invention, and FIG. 5B is a cross sectional view taken along the dotted line V-V in FIG. 5A. The capillary array 1 is secured to an aluminum plate 31 via epoxy series adhesive 34. Further, in order to ensure an electrical insulation between the inside of the capillaries and the surface of the aluminum plate 31 a polyimide sheet 33 having thickness of 25 μm is adhered on the aluminum plate 31. However, if the above epoxy series adhesive itself shows a necessary insulative property, the insulation sheet 33 can be omitted. Even in the region between the detection portion 8 and the gel block connection terminal 5 the capillaries are also secured to the aluminum plate 31 by making use of the epoxy series adhesive. The capillary array with the aluminum plate 31 is secured by means of securing members 32 in a space "a" of the thermostatic oven 11 provided with a heating and cooling device 30 such as Peltier elements and fans 38 and 39. As a result of the same measurement as a comparison example 1 with the present capillary array, the COP value was 360 bases. According to the present embodiment, an enhancement in resolution of more than 100 bases can be achieved in comparison with the capillary array with no heat dissipation measure over the entire capillaries and at and near the gel supply portion 5.

Embodiment 4

Figure 6:
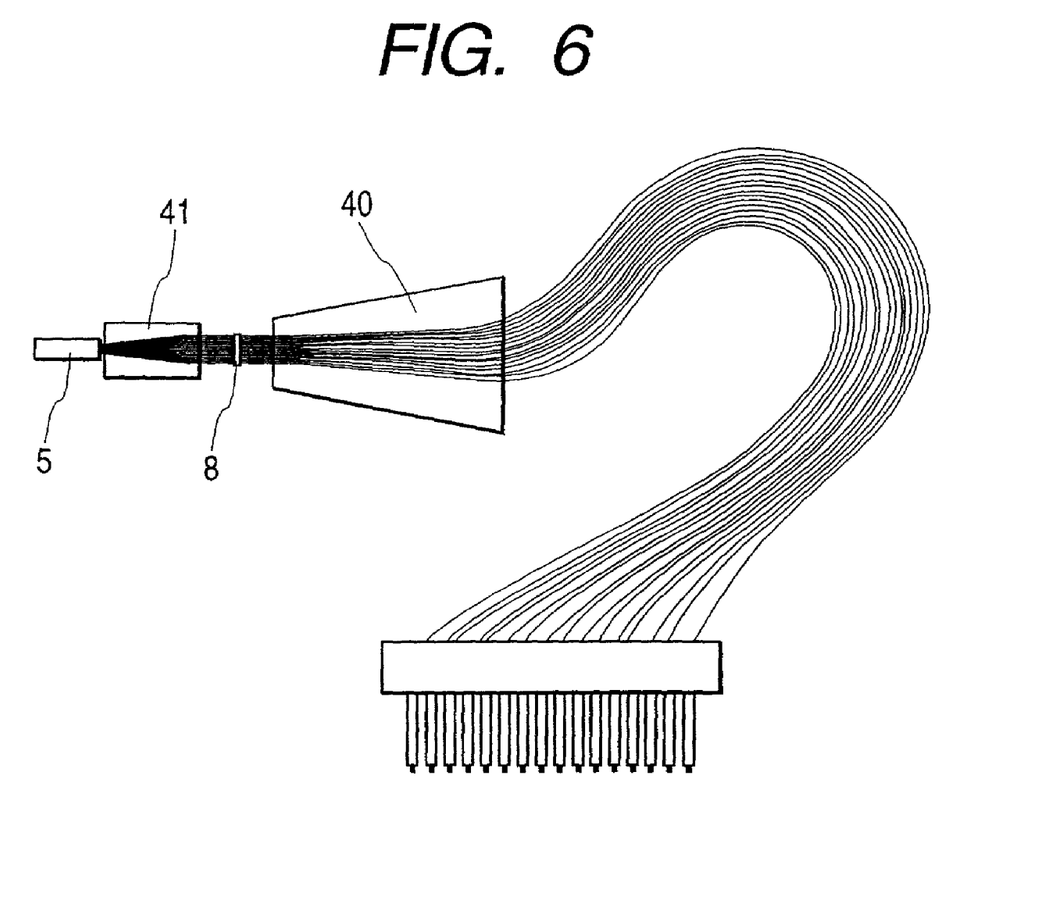
FIG. 6 is a schematic view of a capillary array of an embodiment 4 of the present invention.

FIG. 6 shows a capillary array of the embodiment 4 according to the present invention. A different point from the embodiment 3 is that the aluminum plate is not provided for the entire capillaries, but an aluminum plate 40 is provided near the protective portion 8 and in a region of 5 cm length where the capillaries gather collectively toward the cathode side (the sample introduction side) and is secured with an epoxy series adhesive, and for the capillaries in the region from the detection portion 8 to the gel block connection terminal 5 an aluminum plate 41 is secured with the epoxy series adhesive. When the both aluminum plates 40 and 41 and attached, the COP value was 340 bases. According to the present embodiment, an enhancement in resolution of about 90 bases can be achieved in comparison with the capillaries with no heat dissipation measure.

Further, when only the aluminum plate 41 is attached, the COP value was 300 bases. Even in this instance, an enhancement in resolution of about 50 bases can be achieved in comparison with the capillaries with no heat dissipation measure.

Embodiment 5

Figure 7A:
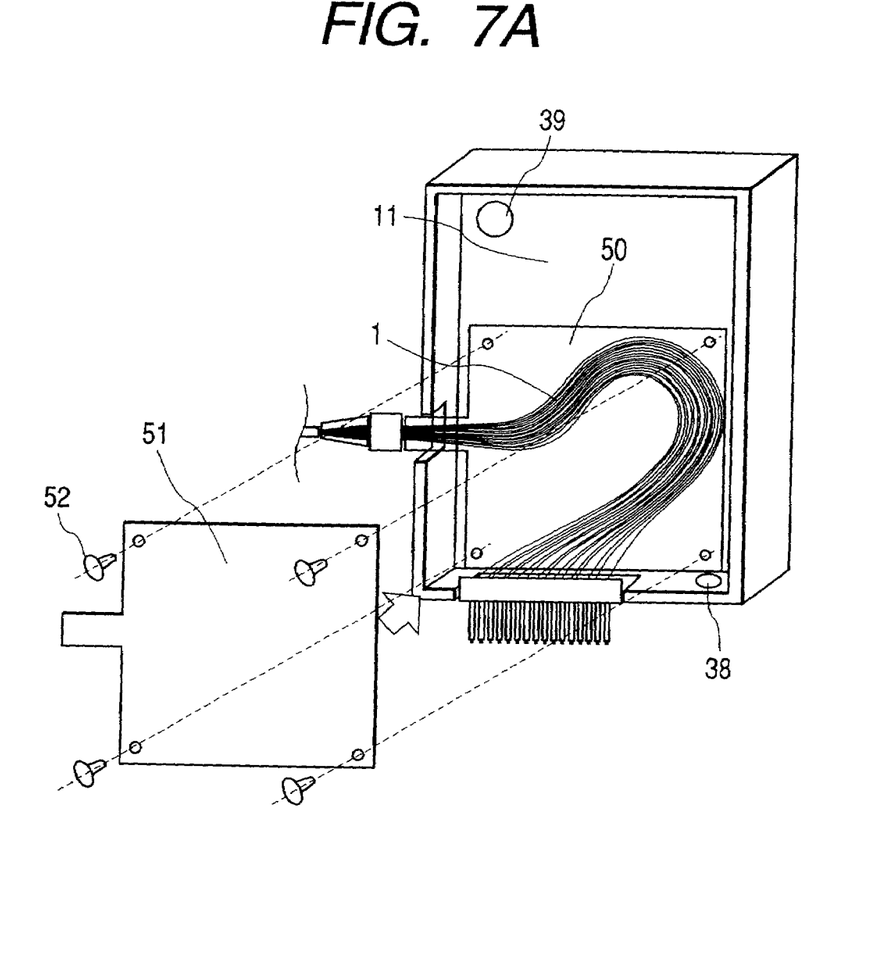
FIG. 7A is a front view of a thermostatic oven portion and a capillary array of an electrophoresis apparatus representing an embodiment 5 of the present invention and FIG. 7B is a cross sectional view thereof.
Figure 7B:
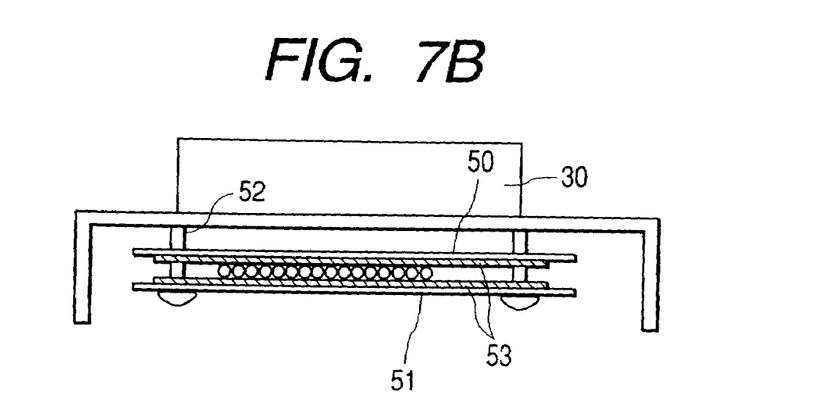

FIG. 7A shows a front view of an electrophoresis apparatus (illustrating only the thermostatic oven 11) and a capillary array representing an embodiment 5 according to the present invention and FIG. 7B is a cross sectional view thereof. Other than attaching the capillary array 1 on to an aluminum plate 50 with such as an adhesive, the capillaries are sandwiched with a cover aluminum plate 51 via a heat conductive rubber sheets 53 by means of screw 52. The heat conductive rubber sheets 53 and the aluminum plates 50 and 51 are a part of the electrophoresis apparatus. When the thus constituted electrophoresis apparatus and capillary array is used, the COP value was 340 bases. According to the present embodiment, an enhancement in resolution of about 100 bases can be achieved in comparison with the capillary array with no heat dissipation measure.

According to the present invention, the heat generated from the capillaries can be efficiently removed, thereby, detection error between capillaries is reduced and efficiency of electrophoresis is enhanced.

The invention claimed is:

1. An electrophoresis apparatus comprising:
   a capillary array including a plurality of capillaries coated by a protective polymer film and having a sample supply portion, a gel supply portion and a detection portion to which light is irradiated;
   a thermostatic oven in which at least a part of the capillary array is disposed; and
   a high thermal conductivity body which contacts substantially the entire length of the capillaries located outside of the thermostatic oven and between the gel supply portion and the detection portion, wherein the high thermal conductivity body contacts the capillaries coated by the protective polymer film via an elastic polymer material, wherein the elastic polymer material surrounds the capillaries and the protective polymor film located outside of the thermostatic oven and between the gel supply portion and the detection portion, and wherein both the high thermal conductivity body and the elastic polymer material are integral with the thermostatic oven.

2. An electrophoresis apparatus according to claim 1, wherein the high thermal conductivity body is selected from the group consisting of a metal, a polymer material containing an inorganic filler, and an inorganic material.

3. An electrophoresis apparatus according to claim 1, wherein the high thermal conductivity body is a polymer material containing inorganic powders or metal powders.

4. The electrophoresis apparatus of claim 1, wherein the elastic polymer material comprises a heat conductive rubber sheet.

5. An electrophoresis apparatus comprising:
a capillary array including a plurality of capillaries coated by a protective polymer film and having a sample supply portion, a gel supply portion and a detection portion to which light is irradiated;
a thermostatic oven in which at least a part of the region between the sample supply portion and the detection portion in the capillary array is disposed; and
a high thermal conductivity body selected from the group consisting of a metal, a polymer material containing an inorganic filler, and an inorganic material, the high thermal conductivity body contacting at least a part of the capillary array existing outside the thermostatic oven via an elastic polymer material, wherein the elastic polymer material surrounds the capillaries and the protective polymer film existing outside of the thermostatic oven, and wherein both the high thermal conductivity body and the elastic polymer material are integral with the thermostatic oven.

6. The electrophoresis apparatus of claim 5, wherein the elastic polymer material comprises a heat conductive rubber sheet.

7. An electrophoresis apparatus comprising:
a capillary array including a plurality of capillaries coated by a protective polymer film and having a spaced apart region in which the plurality of capillaries are spaced apart and a crowded region in which the plurality of capillaries contact or come close to each other;
a thermostatic oven in which at least a part of the spaced apart region in the capillary array is disposed; and
a high thermal conductivity body which contacts at least a part of the crowded region in the capillary array existing outside the thermostatic oven via an elastic polymer material, wherein the elastic polymer material surrounds the capillaries and the protective polymer film existing outside of the thermostatic oven, and wherein both the high thermal conductivity body and the elastic polymer material are integral with the thermostatic oven.

8. An electrophoresis apparatus according to claim 7, wherein the high thermal conductivity body is selected from the group consisting of a metal, a polymer material containing an inorganic filler, and an inorganic material.

9. An electrophoresis apparatus according to claim 7, wherein the high thermal conductivity body is a polymer material containing inorganic powders or metal powders.

10. The electrophoresis apparatus of claim 7, wherein the elastic polymer material comprises a heat conductive rubber sheet.

11. A method of electrophoresis comprising the steps of:
preparing a capillary array including a plurality of capillaries coated by a protective polymer film and having a sample supply portion, a gel supply portion and a detection portion to which light is irradiated;
introducing a sample into the capillaries; and
subjecting the sample to electrophoresis, while exposing at least a part of the capillary array to a temperature regulated gas and contacting a high thermal conductivity body to substantially the entire length of the capillaries not exposed to the temperature regulated gas located between the gel supply portion and the detection portion in the capillary array, wherein the high thermal conductivity body contacts the capillaries coated by the protective polymer film via an elastic polymer material, wherein the elastic polymer material surrounds the capillaries and the protective polymer film located outside of the thermostatic oven and between the gel supply portion and the detection portion, and wherein both the high thermal conductivity body and the elastic polymer material are integral with the thermostatic oven.

12. A method of electrophoresis according to claim 11, wherein the high thermal conductivity body is selected from the group consisting of a metal, a polymer material containing an inorganic filler, and an inorganic material.

13. A method of electrophoresis according to claim 11, wherein the high thermal conductivity body is a polymer material containing inorganic powders or metal powders.

14. The method of claim 11, wherein the elastic polymer material comprises a heat conductive rubber sheet.

15. A method of electrophoresis comprising the steps of:
preparing a capillary array including a plurality of capillaries coated by a protective polymer film and having a sample supply portion, a gel supply portion and a detection portion to which light is irradiated;
introducing a sample into the capillaries; and
subjecting the sample to electrophoresis while disposing at least a part of the region between the sample supply portion and the detection portion in the capillary array in a thermostatic oven and contacting at least a part of the capillary array existing outside the thermostatic oven to a high thermal conductivity body via an elastic polymer material, wherein the high thermal conductivity body is selected from the group consisting of a metal, a polymer material containing an inorganic filler, and an inorganic material, and wherein the elastic polymer material surrounds the capillaries and the protective polymer film existing outside of the thermostatic oven, and wherein both the high thermal conductivity body and the elastic polymer material are integral with the thermostatic oven.

16. The method of claim 15, wherein the elastic polymer material comprises a heat conductive rubber sheet.

17. A method of electrophoresis comprising the steps of:
preparing a capillary array including a plurality of capillaries coated by a protective polymer film and having a spaced apart region in which the plurality of capillaries are spaced apart and a crowded region in which the plurality of capillaries contact or come close to each other;
introducing a sample into the capillaries; and
subjecting the sample to electrophoresis, while disposing at least a part of the spaced apart region in the capillary array in a thermostatic oven and contacting at least a part of the crowded region in the capillary array existing outside the thermostatic oven to a high thermal conductivity body via an elastic polymer material, wherein the elastic polymer material surrounds the capillaries and the protective polymer film existing outside of the thermostatic oven, and wherein both the high thermal conductivity body and the elastic polymer material are integral with the thermostatic oven.

18. A method of electrophoresis according to claim 17, wherein the high thermal conductivity body is selected from the group consisting of a metal, a polymer material containing an inorganic filler, and an inorganic material.

19. A method of electrophoresis according to claim 17, wherein the high thermal conductivity body is a polymer material containing inorganic powders or metal powders.

20. The method of claim 17, wherein the elastic polymer material comprises a heat conductive rubber sheet.

* * * * *